United States Patent [19]

Kleemann et al.

[11] 4,161,491

[45] Jul. 17, 1979

[54] PROCESS FOR THE PRODUCTION OF ALPHA-KETOCARBOXYLIC ACID AMIDES AND CYCLOALIPHATIC PRODUCTS

[75] Inventors: Axel Kleemann; Herbert Klenk, both of Hanau; Werner Schwarze, Frankfurt, all of Fed. Rep. of Germany

[73] Assignee: Deutsche Gold- und Silber-Scheideanstalt vormals Roessler, Frankfurt, Fed. Rep. of Germany

[21] Appl. No.: 802,903

[22] Filed: Jun. 2, 1977

[30] Foreign Application Priority Data

Feb. 25, 1977 [DE] Fed. Rep. of Germany ....... 2708184

[51] Int. Cl.² .................. C07C 102/02; C07C 102/08; C07C 103/19; C07C 103/127
[52] U.S. Cl. .............................. 260/557 R; 260/404; 260/561 K
[58] Field of Search ................ 260/557 R, 561 K, 404

[56] References Cited

U.S. PATENT DOCUMENTS 2,434,507  1/1948  Mostek .................... 260/561 K X

OTHER PUBLICATIONS

Birchall et al., Cun. J. Chem. 49, 919 (1971)–Abstract.
Oakwood et al., Org. Synth. 24, 16 (1944)–Abstract.
Claisen et al., Berichte 13, 2121 (1880).
Moritz, J. Chem. Soc. (London) 39, 13-19 (1881).
Patai, ed., The Chemistry of Amides, pp. 120–121, (1970).

*Primary Examiner*—Thomas Waltz
*Attorney, Agent, or Firm*—Cushman, Darby & Cushman

[57] ABSTRACT

There are prepared α-ketocarboxylic acid amides of the formula $$R_1-\underset{\underset{R_2}{|}}{\overset{R}{\overset{|}{C}}}-\overset{O}{\overset{\|}{C}}-\overset{O}{\overset{\|}{C}}-NH_2 \quad (I)$$

where R is hydrogen, $R_1$ and $R_2$ are the same or different, $R_1$ is alkyl of 1 to 18 carbon atoms or haloalkyl, preferably chloroalkyl, of 1 to 18 carbon atoms, and $R_2$ is hydrogen, alkyl of 1 to 18 carbon atoms or haloalkyl, preferably chloroalkyl, of 1 to 18 carbon atoms or $$\underset{\underset{R_2}{|}}{\overset{R_1-C}{\overset{|}{}}}$$

together is a cycloalkyl group of 3 to 8 carbon atoms which can be substituted by one or more 1 to 5 carbon atom alkyl groups or by one or more halogen atoms, preferably chlorine atoms, with the proviso that when $$\underset{\underset{R_2}{|}}{\overset{R_1-C}{\overset{|}{}}}$$

form a cycloalkyl group then R can also be alkyl of 1 to 5 carbon atoms. The process comprises saponifying an acyl cyanide of the formula $$R_1-\underset{\underset{R_2}{|}}{\overset{R}{\overset{|}{C}}}-\overset{O}{\overset{\|}{C}}-CN \quad (II)$$

in which R, $R_1$ and $R_2$ are as defined above in an organic solvent or mixture of such solvents which is liquid and inert under the reaction conditions, first with gaseous hydrogen chloride and then treating with water at a temperature of about −70° C. to about +70° C. and then isolating the α-ketocarboxylic acid amide in conventional manner. Several of the cyclic α-ketocarboxylic acid amides are new compounds.

32 Claims, No Drawings

PROCESS FOR THE PRODUCTION OF ALPHA-KETOCARBOXYLIC ACID AMIDES AND CYCLOALIPHATIC PRODUCTS

BACKGROUND OF THE INVENTION

The invention is directed to a process for the production of aliphatic and cycloaliphatic α-ketocarboxylic acid amides by partial saponification of acyl cyanides. These α-ketocarboxylic acid amides are useful as intermediate products for the synthesis of pharmacologically important hydroxy quinoxalines.* They also can be hydrolyzed further to the corresponding free acids which can be used as disclosed in our application Ser. No. 802,899, filed on even date and claiming the priority of German application P 27 08 185.2. *

*For this purpose the amides are hydrolized to the ketocarbonic acids and then condensed with o-phenylene-diamines.

Previously such α-ketocarboxylic acid amides have been produced from acyl cyanides by careful treatment of the cyanide with fuming hydrochloric acid (L. Claisen, E. Moritz, Ber. deutsch. Chem. Ges. 13 (1880) page 2121). The disadvantage of this process is that very small yields are obtained. Thus in the saponification of butyryl cyanide there is only a yield of 12% and in the saponification of isobutyryl cyanide there is only found a yield of about 3% of the corresponding amide (E. Moritz, J. Chem. Soc. 39 (1881) pages 13 to 19, particularly 13 and 16.

SUMMARY OF THE INVENTION

It has now been found that there can be prepared in high yields α-ketocarboxylic acid amides of the formula

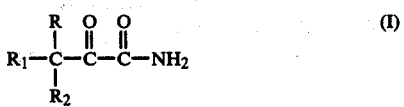

(I)

where R is hydrogen, $R_1$ and $R_2$ are the same or different, $R_1$ is alkyl of 1 to 18 carbon atoms or haloalkyl, preferably chloroalkyl, of 1 to 18 carbon atoms, $R_2$ is hydrogen, alkyl of 1 to 18 carbon atoms or haloalkyl, preferably chloroalkyl of 1 to 18 carbon atoms or

together is a cycloalkyl group of 3 to 8 carbon atoms which can have one or more 1 to 5 carbon atom alkyl substituents and/or one or more halogen atom, preferably chlorine atom, substituents, with the proviso that when

form a cycloalkyl group then R can also be alkyl of 1 to 5 carbon atoms. Usually the total carbon atoms in

when it is not cycloalkyl is 2 to 18 carbon atoms, more usually 2 to 10 carbon atoms. When

is cycloalkyl then the alkyl substituents, if present, usually have 1 to 3 carbon atoms and more preferably are methyl. The process comprises saponifying an acyl cyanide of the formula

(II)

in which R, $R_1$ and $R_2$ are as defined above in an organic solvent which is liquid and inert under the reaction conditions (or a mixture of such solvents), first with gaseous hydrogen chloride and then with water at a temperature of about −70° C. to about +70° C. and isolating the carboxylic acid amide in known manner.

Within the scope of the invention there are preferably produced compounds in which

forms a cyclopropyl group. Especially preferred are compounds where the cyclopropyl group is substituted by one or two halogen atoms, especially chlorine.

The production of the acyl cyanides used as starting materials is described, for example, in Houben-Weyl, Methoden der Organ. Chemie, 8, 304–306. However, they call also be obtained in a more advantageous manner by reaction of the corresponding acyl halide with CuCN in a mixture of 1 to 10 parts by weight of an inert carboxylic acid nitrile and 0.5 to 20 parts by weight of an inert organic solvent at a temperature between 50° and 180° C. This procedure is disclosed in more detail in Klenk et al. application Serial No. 802,944, filed on even date, now U.S. Pat. No. 4,108,877, and claiming the priority of German application 27 08 183.9. The entire disclosure of the Klenk et al. U.S. application is hereby incorporated by reference and relied upon. This reaction can also be carried out in the presence of a mixture of 0.1 to 5 parts by weight of an alkali metal cyanide and 0.05 to 2 parts by weight of a copper (I) salt in place of the CuCN. This procedure is disclosed in more detail in Klenk et al. application Serial No. 802,942, filed on even date, now U.S. Pat. No. 4,108,875, and claiming the priority of German application 27 08 182.9. The entire disclosure of this second Klenk et al. U.S. application is also hereby incorporated by reference and relied upon.

Examples of compounds within the invention are α-oxo-isovaleric acid amide, α-oxo-isocapronamide, D,L-3-methyl-2-oxo-valeramide, 5-chloro-2-oxo-valeramide, cyclopropyl glyoxalic acid amide, (2,2-dichloro-1-methylcyclopropyl)-glyoxylic acid amide, (2,2-dichloro-1,3-dimethylcyclopropyl)-glyoxylic acid amide, 2-methylcyclopropyl glyoxylic acid amide, 2,2-dimethylcyclopropyl glyoxylic acid amide, cyclohexyl-gloxylic acid amide, cyclooctyl glyoxylic acid amide, 2,2-dichlorocyclopropyl glyoxylic acid amide, 2-chlorocyclopropyl glyoxylic acid amide, (2,2-dibromo- 1,3-dimethylcyclopropyl)-glyoxylic acid amide, 5-bromo-2-oxovaleramide, 4-chloro-2-oxobutyramide, 2-oxovaleramide, 2-oxoisodecanoamide, 2-oxostearamide, 2-oxopropionamide, 3-butyl-2-oxocapronamide.

As the starting acyl cyanides there can be used any which come within formula (II), e.g., isobutyryl cyanide, isovaleroyl cyanide, 2-methylbutyryl cyanide, 4-chlorobutyryl cyanide. cyclopropanoyl cyanide, (2,2-dichloro-1-methylcyclopropyl)-glyoxylic acid nitrile, (2,2-dichloro-1,3-dimethylcyclopropyl)-glyoxylic acid nitrile, 2,2-dimethylcyclopropyl-glyoxylic acid nitrile, 4-bromobutyryl cyanide, 2-oxoisononanoyl nitrile and 2-oxoheptadecanoyl nitrile.

As inert organic solvents there can be used, for example, hydrocarbons, e.g., aromatic hydrocarbons such as benzene, toluene or xylene as well as mesitylene, ethyl benzene, cumene, p-cymene, t-butyl benzene or 1,3,5-triethyl benzene or aliphatic hydrocarbons such as ligroin with a boiling range of about 90° to 140° C., pentane, hexane, heptane, octane or decane or cyclic hydrocarbons such as decalin or cyclohexane or halogenated hydrocarbons, particularly chlorinated aromatic or aliphatic hydrocarbons such as chlorobenzene, dichlorobenzene, symmetrical tetrachloroethane, chloroform, carbon tetrachloride, trichloroethylene, methylene chloride, trimethylene bromide, dibromethylene, ethylene dibromide or dichloroethylene. Especially suited are both open chain and cyclic ethers, e.g., dioxane, dibutyl ether, diisopropyl ether, ethylene glycol diethyl ether, ethylene glycol dibutyl ether, ethylene glycol dimethyl ether. There can also be used ketones, e.g., acetone and methyl ethyl ketone. Mixtures of solvents can be used.

The amount of solvent is not critical. It is usually employed in an amount of 50 to 1000 ml per mole of acyl cyanide.

The treatment is carried out with water at a temperature between −70° C. and +70° C. It is particularly advantageous to keep the temperature between −40° C. and +20° C. The water can be added to the mixture at temperatures below 0° C. because it is soluble in the solvent. Also, the water can be added dropwise to the already cold mixture and the water reacts promptly.

Furthermore, it is advantageous to carry out the treatment with the hydrogen chloride gas in this same temperature range.

Although there can be used for the reaction large amounts of excess gaseous hydrogen chloride, it is generally suitable to use not more than 10 moles of hydrogen chloride per mole of acyl cyanide. For example, there can even be used one mole or less of hydrogen chloride per mole of acyl cyanide. It is only essential that hydrogen chloride be present. Favorable results are obtained using about 2 to about 6 moles of hydrogen chloride per mole of acyl cyanide.

For the complete reaction of one mole of acyl cyanide to α-ketocarboxylic acid amide (α-ketocarbonamide) it is necessary to use at least one mole of water. It is also possible to employ a large excess of water. For example, there can be employed an excess of 0.05 to 5 moles, especially of 0.05 to 1 mole of water per mole of acyl cyanide.

The α-ketocarbonamides can be recovered in simple manner by concentration of the solvent and crystallization or by neutralization of the excess hydrochloric acid and extraction by a solvent. They can be purified by distillation or preferably by recrystallization.

Some of the α-ketocarboxylic acid amides made by the process of the invention have not previously been described in the literature. They have the formula

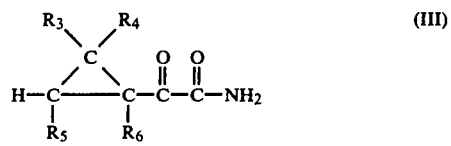

in which $R_3$, $R_4$, $R_5$ and $R_6$ are the same or different, $R_5$ and $R_6$ are hydrogen or alkyl with 1 to 5 carbon atoms and $R_3$ and $R_4$ are hydrogen, alkyl with 1 to 5 carbon atoms or chlorine. The preferred alkyl group is methyl.

In addition to the uses mentioned above, the compounds of formula III can also be used too.

DESCRIPTION OF THE PREFERRED EMBODIMENTS

EXAMPLE 1

In an apparatus equipped with a stirrer and a gas inlet tube and protected against moisture there were placed 97.1 grams (1.0 mole) of isobutyryl cyanide and 250 ml of ethylene glycol dimethyl ether and the apparatus cooled to −30° C. Then a strong flow of gaseous HCl was led in until 146 grams (4.0 moles) were introduced. Then 21.6 grams (1.2 moles) of water were dropped in during 10 minutes and the temperature raised to 0° C. during 2 hours with stirring. Then a strong flow of $N_2$ was led in and the excess hydrogen chloride driven off. The solution was subsequently evaporated at 40° C. in a water jet vacuum whereupon a yellowish crystal sludge remained behind. This was recrystallized from ligroin-benzene and the crystals obtained dried at 40° C. in a vacuum. There were obtained 92.5 of α-oxoisovaleramide which corresponds to a yield of 80% based on the acyl cyanide employed. The amide had a melting point of 107° to 108° C.

EXAMPLE 2

The procedure was the same as in Example 1 except that there was used as the solvent 300 ml of acetone and only 19.6 grams (1.1 mole) of water were dropped in. There were isolated 86.5 grams of α-oxoisovaleramide which corresponds to a yield of 75% based on the acyl cyanide employed. The amide had a melting point of 106.5° to 107.5° C.

EXAMPLE 3

The procedure was the same as in Example 1 except that there were employed 111.1 grams (1.0 mole) of isovaleroyl cyanide in place of isobutyryl cyanide and in place of ethylene glycol dimethyl ether as the solvent there was employed diethyl ether. After recrystallization from water there were isolated 117.5 grams of α-oxoisocapronamide which corresponds to a yield of 91% based on the acyl cyanide employed. The amide had a melting point of 79° to 79.5° C.

EXAMPLE 4

The procedure was the same as that in Example 1 except that in place of isobutyryl cyanide there were employed 111.1 grams (1.0 mole) of D,L-2-methylbutyryl cyanide and in place of ethylene glycol dimethyl ether there was used a mixture of 100 ml of toluene and 200 ml of diisopropyl ether. After recrystallization from water there were isolated 110 grams of D,L-3-methyl-2- oxovaleramide which correspond to a yield of 85.5% based on the acyl cyanide employed. The amide had a melting point of 67° to 69° C.

EXAMPLE 5

The procedure was the same as that described in Example 1 except that instead of isobutyryl cyanide there were employed 131.5 grams (1.0 mole) of 4-chlorobutyryl cyanide. After recrystallization from water there were isolated 130 grams (87% of theory) of 5-chloro-2-oxovaleramide having a melting point of 87° C.

C$_5$H$_8$ClNO$_2$ (Molecular Weight 149.5)
Calculated: C 40.1%; H 5.4%; N 9.4%, Cl 23.7%
Found: C 40.01%; H 5.49%; N 9.22%; Cl 23.74%

EXAMPLE 6

The procedure was the same as that described in Example 1 except that instead of isobutyryl cyanide there were used 95 grams (1.0 mole) of cyclopropanoyl cyanide and the process was modified as indicated below. Dimethylether was used as the solvent. After the temperature had reached 0° C. there was dropped into the solution at a temperature of 0° to 10° C. dilute NaOH solution until the aqueous phase had a pH of 8. Then the organic phase was separated and evaporated in a vacuum. The white residue was recrystallized from water and dried in a vacuum at 40° C. There were isolated 97.5 grams of cyclopropylglyoxylic acid amide having a melting point of 111° to 112° C. This corresponds to a yield of 87.5% based on the acyl cyanide employed.

C$_5$H$_7$NO$_2$ (Molecular Weight 113)
Calculated: C 53.1%; H 6.24%; N 12.39%;
Found: C 52.7%; H 6.4%; N 12.25%.

EXAMPLE 7

The procedure was the same as in Example 6 except that instead of cyclopropanoyl cyanide there were employed 178 grams (1.0 mole) of (2,2-dichloro-1-methylcyclopropyl)-glyoxylic acid nitrile. After recrystallization from ethyl acetate there were obtained 168 grams (85.7% of theory) of (2,2-dichloro-1-methylcyclopropyl)-glyoxylic acid amide having a melting point of 92° to 93° C.

C$_6$H$_7$Cl$_2$NO$_2$ (Molecular Weight 196)
Calculated: C 36.73%; H 3.6%; N 7.15%; Cl 36.2%;
Found: C 36.92%; H 3.7%; N 7.2%; Cl 35.9%.

EXAMPLE 8

The procedure was the same as in Example 6 except that instead of cyclopropanoyl cyanide there were used 192 grams (1.0 mole) of (2,2-dichloro-1,3-dimethylcyclopropyl)glyoxylic acid nitrile. There were isolated 201 grams of (2,2-dichloro-1,3-dimethylcyclopropyl)-glyoxylic acid amide which corresponds to a yield of 94.8% based on the acyl cyanide employed. The amide had a melting point of 87° to 89° C.

What is claimed is:

1. A process for the production of α-ketocarboxylic acid amides of the formula

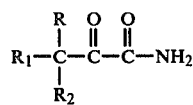

(I)

where R is hydrogen, R$_1$ is alkyl of 1 to 18 carbon atoms or haloalkyl of 1 to 18 carbon atoms, R$_2$ is hydrogen, alkyl of 1 to 18 carbon atoms or haloalkyl of 1 to 18 carbon atoms or

together is a cycloalkyl group of 3 to 8 carbon atoms or such a cycloalkyl group substituted by at least one alkyl group of 1 to 5 carbon atoms or by at least one halogen atom comprising saponifying an acyl cyanide of the formula

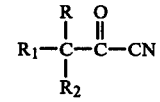

(II)

in a liquid organic solvent inert under the reaction conditions, first with gaseous hydrogen chloride and then with water at a temperature of about −70° C. to about +70° C.

2. The process of claim 1 wherein any halogen atom present is chlorine and there is included the step of isolating the ketocarboxylic acid amide.

3. The process of claim 2 wherein when

is not cycloalkyl it has 2 to 18 carbon atoms and when it is cycloalkyl it has 3 to 6 carbon atoms in the ring.

4. The process of claim 2 wherein R is hydrogen, R$_1$ is alkyl of 1 to 18 carbon atoms or chloroalkyl of 1 to 18 carbon atoms and R$_2$ is hydrogen, alkyl of 1 to 18 carbon atoms or chloroalkyl of 1 to 18 carbon atoms.

5. The process of claim 4 wherein the total carbon atoms in

is 2 to 18.

6. The process of claim 5 wherein the total carbon atoms in

is 2 to 10.

7. The process of claim 5 wherein R$_1$ is alkyl and R$_2$ is hydrogen or alkyl.

8. The process of claim 7 wherein

has 3 to 4 carbon atoms.

9. The process of claim 7 wherein the compound of formula (I) is α-oxoisovaleramide, α-oxoisocapronamide or 3-methyl-2-oxovaleramide.

10. The process of claim 5 wherein $R_1$ is chloroalkyl and $R_2$ is hydrogen or alkyl.

11. The process of claim 10 wherein $R_2$ is hydrogen.

12. The process of claim 11 wherein the compound of formula (I) is 5-chloro-2-oxovaleramide.

13. The process of claim 3 wherein the compound of formula (I) has a cycloalkyl group.

14. The process of claim 13 wherein the cycloalkyl group has 3 to 6 carbon atoms.

15. The process of claim 14 wherein the compound of formula (I) has the formula

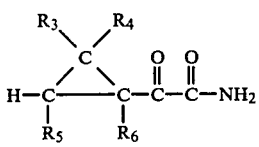 (III)

wherein $R_5$ and $R_6$ are hydrogen or alkyl with 1 to 5 carbon atoms and $R_3$ and $R_4$ are hydrogen, alkyl with 1 to 5 carbon atoms or chlorine.

16. The process of claim 15 wherein any alkyl group present is methyl.

17. The process of claim 15 wherein $R_3$, $R_4$, $R_5$ and $R_6$ are hydrogen.

18. The process of claim 15 wherein $R_3$ and $R_4$ are chlorine.

19. The process of claim 18 wherein $R_6$ is methyl and $R_5$ is hydrogen or methyl.

20. The process of claim 1 wherein there are employed 1 to 10 moles of hydrogen chloride gas per mole of acyl cyanide.

21. The process of claim 20 wherein there are employed 2 to 6 moles of hydrogen chloride gas per mole of acyl cyanide.

22. The process of claim 21 wherein there are employed 1.05 to 2 moles of water per mole of acyl cyanide.

23. The process of claim 20 wherein there are employed 1.05 to 6 moles of water per mole of acyl cyanide.

24. An α-ketocarboxylic acid amide of the formula

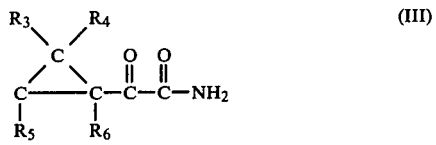 (III)

wherein $R_5$ and $R_6$ are hydrogen or alkyl with 1 to 5 carbon atoms and $R_3$ and $R_4$ are hydrogen, alkyl with 1 to 5 carbon atoms or chlorine.

25. The compound of claim 24 wherein $R_5$ and $R_6$ are hydrogen or alkyl with 1 to 3 carbon atoms and $R_3$ and $R_4$ are hydrogen, alkyl with 1 to 3 carbon atoms or chlorine.

26. The compound of claim 25 wherein $R_5$ and $R_6$ are hydrogen or methyl and $R_3$ and $R_4$ are hydrogen, methyl or chlorine.

27. The compund of claim 26 wherein $R_3$ and $R_4$ are chlorine.

28. The compound of claim 24 wherein $R_3$ and $R_4$ are chlorine.

29. The process of claim 1 wherein the solvent is a hydrocarbon, halohydrocarbon, ketone or ether.

30. The process of claim 21 wherein there is employed at least 1 mole of water per mole of acyl cyanide.

31. The process of claim 20 wherein there is employed at least 1 mole of water per mole of acyl cyanide.

32. The process of claim 1 wherein there is employed at least 1 mole of water per mole of acyl cyanide.

* * * * *